(12) United States Patent
Edwards et al.

(10) Patent No.: US 9,752,964 B1
(45) Date of Patent: Sep. 5, 2017

(54) FLOW CYTOMETRY APPARATUS PULLING SAMPLE STREAM THROUGH OBSERVATION CHAMBER

(71) Applicant: STC.UNM, Albuquerque, NM (US)

(72) Inventors: Bruce S. Edwards, Albuquerque, NM (US); Larry A. Sklar, Albuquerque, NM (US); Ronald D. Salesky, Rio Rancho, NM (US)

(73) Assignee: STC.UNM, Albuquerque, NM (US)

( * ) Notice: Subject to any disclaimer, the term of this patent is extended or adjusted under 35 U.S.C. 154(b) by 664 days.

(21) Appl. No.: 13/717,279

(22) Filed: Dec. 17, 2012

Related U.S. Application Data

(62) Division of application No. 12/802,880, filed on Jun. 16, 2010, now abandoned.

(60) Provisional application No. 61/269,265, filed on Jun. 22, 2009.

(51) Int. Cl.
  *G01N 21/00* (2006.01)
  *G01N 15/06* (2006.01)
  *G01N 33/00* (2006.01)
  *G01N 1/14* (2006.01)

(52) U.S. Cl.
  CPC ..................... *G01N 1/14* (2013.01)

(58) Field of Classification Search
  CPC .......... B01L 3/5085; B01L 2300/0867; B01L 2400/0487; B01L 3/502776; B01L 3/0293; G01N 2015/1413; G01N 2015/149; G01N 35/0099; G01N 35/085; G01N 35/1095; G01N 15/1459; G01N 2015/1402; G01N 2015/1477; G01N 15/1404; G01N 35/08; G01N 15/1484; G01N 1/38; G01N 2015/1018; G01N 2015/1409; G01N 2035/00514; G01N 2035/00544; G01N 2500/10; G01N 33/543; G01N 33/54313; G01N 33/54393; G01N 35/1011; G01N 35/1074
  USPC ........................................... 422/62–68.1, 73
  See application file for complete search history.

(56) References Cited

U.S. PATENT DOCUMENTS

| | | |
|---|---|---|
| 3,698,870 A | 10/1972 | DeJong |
| 3,921,439 A | 11/1975 | Burns |
| 4,053,282 A | 10/1977 | Hach et al. |
| 4,116,631 A | 9/1978 | Trinel et al. |
| 4,177,677 A | 12/1979 | Ruzicka et al. |
| 4,224,033 A | 9/1980 | Hansen et al. |

(Continued)

OTHER PUBLICATIONS

U.S. Appl. No. 61/269,265, filed Jun. 2009, Bruce Edwards.

(Continued)

*Primary Examiner* — Dean Kwak
(74) *Attorney, Agent, or Firm* — R. Neil Sudol; Henry D. Coleman

(57) ABSTRACT

A flow cytometry apparatus includes a flow cytometer having a suction or negative-pressure intake probe, a support for a microplate having a plurality of sample wells, and motive elements operatively connected to at least one of the probe and the support for moving the intake probe and the support relative to one another so that the intake probe is sequentially aligned with different sample wells of the microplate. The apparatus has no fluid pumping elements between the support and the flow cytometer so that a bubble-separated sample stream is forced to the flow cytometer solely by virtue of a negative pressure communicated via the intake probe.

6 Claims, 5 Drawing Sheets

(56) References Cited

U.S. PATENT DOCUMENTS

| | | | |
|---|---|---|---|
| 4,399,225 | A | 8/1983 | Hansen et al. |
| 4,661,913 | A | 4/1987 | Wu et al. |
| 4,853,336 | A | 8/1989 | Saros et al. |
| 4,957,009 | A | 9/1990 | Nohl et al. |
| 5,080,866 | A | 1/1992 | Petty et al. |
| 5,221,521 | A | 6/1993 | Hashizume et al. |
| 5,268,147 | A | 12/1993 | Zabetakis et al. |
| 5,286,452 | A | 2/1994 | Hansen |
| 5,369,037 | A | 11/1994 | Hansen |
| 5,374,398 | A | 12/1994 | Isami et al. |
| 5,395,588 | A | 3/1995 | North et al. |
| 5,464,752 | A | 11/1995 | Kortright et al. |
| 5,488,469 | A | 1/1996 | Yamamoto et al. |
| 5,504,010 | A | 4/1996 | Mitani et al. |
| 5,532,154 | A | 7/1996 | Brown |
| 5,641,457 | A | 6/1997 | Vardanega et al. |
| 5,694,486 | A | 12/1997 | Shigeeda et al. |
| 5,739,036 | A | 4/1998 | Parris |
| 5,776,781 | A | 7/1998 | Vardanega et al. |
| 5,788,927 | A | 8/1998 | Farrell et al. |
| 5,824,269 | A | 10/1998 | Kosaka et al. |
| 5,834,314 | A | 11/1998 | Gates et al. |
| 6,132,685 | A | 10/2000 | Kercso et al. |
| 6,150,180 | A | 11/2000 | Parce et al. |
| 6,156,178 | A | 12/2000 | Mansfield et al. |
| 6,159,739 | A | 12/2000 | Weigl et al. |
| 6,878,556 | B2 | 4/2005 | Sklar |
| 6,890,487 | B1 | 5/2005 | Sklar |
| 7,354,773 | B2 | 4/2008 | Rubio et al. |
| 7,368,084 | B2 | 5/2008 | Sklar |
| 2005/0123445 | A1* | 6/2005 | Blecka et al. ............... 422/64 |
| 2008/0152542 | A1 | 6/2008 | Ball et al. |
| 2010/0014947 | A1* | 1/2010 | Kehrer et al. ........ 414/222.04 |
| 2010/0105074 | A1 | 4/2010 | Covey et al. |

OTHER PUBLICATIONS

Lindberg et al; "Flow Injection Cytometry: A New Approach for Sample and Solution Handling in Flow Cytometry," Cytometry 14:230-236 (1993).

Pennings et al., "Improved Flow Cytometry of Cellular DNA and RNA by On-Line Reagent Addition," Cytometry 8:335-338 (1987).

Zhao et al., "A Flow Injection Flow Cytometry System for Online Monitoring of Bioreactors," Biotechnology and Bioengineering v62:609-617, Analyst, Biotechnol Biomeg Mar. 1999. (Abstract only).

Deandrade et al., "High Performance Modular Spectrophotometric Flow Cell," Analyst v. 116:905-907, 1991. (Abstract only).

Zhi ZL, "Segmental Flow-Injection Analysis, A Hybrid Technique of Segmented Continuous-Flow Analysis and Flow-Injection Analysis," Analysis, Trac-Trends in Anal. Chem. 17 (7): 411-417 Aug. 1998. (Abstract only).

Hodder, P.S., et al., "Microfabricated Flow Chamber for Fluorescence-Based Chemistries and Stopped-Flow Injection Cytometry," Analyst, vol. 122, pp. 883-887 (Sep. 1997).

Nolan, J.P. et al., "A Rapid Mix Flow Cytometer with Subsecond Kinetic Resolution," Cytometry, vol. 21, pp. 223-229 (1995).

Nolan, J.P., et al., "The Emergence of Flow Cytometry for Sensitive, Real-Time Measurements of Molecular Interactions," Nature Biotechnology, vol. 16, pp. 633-638 (Jul. 1998).

* cited by examiner

FIG. 3A
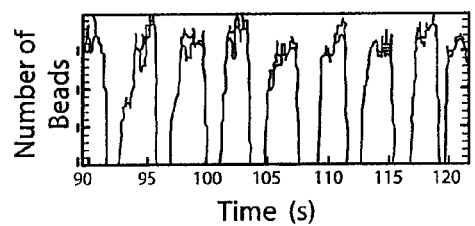
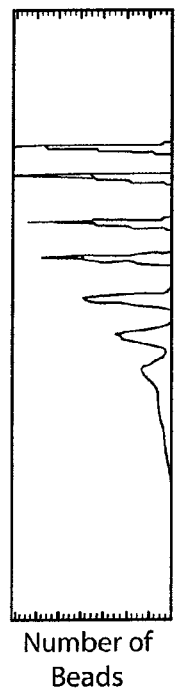
Number of
Beads
FIG. 3B
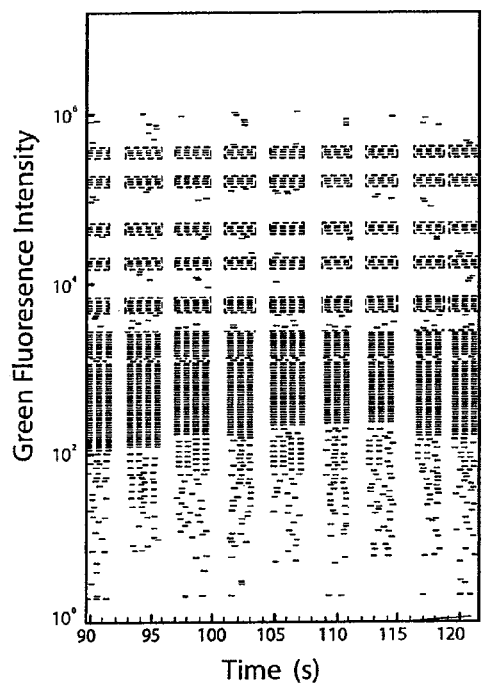
FIG. 3C

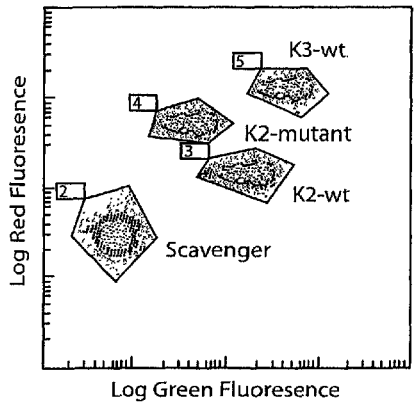
FIG. 5A
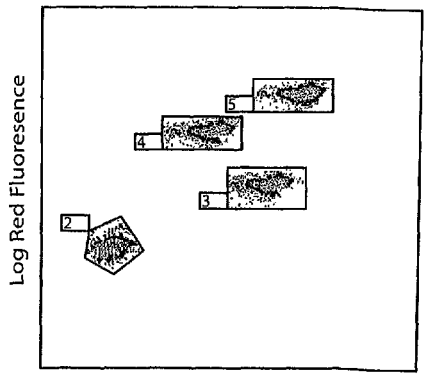
FIG. 5C
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| A | 100 | 100 | 98 | 93 | 98 | 98 | 81 | 94 | 95 | 97 | 93 | 102 | 92 | 103 | 103 | 84 | 101 | 98 | 92 | 100 | 101 | 85 | | |
| B | 100 | 100 | 97 | 93 | 103 | 96 | 96 | 101 | 100 | 96 | 94 | 96 | 92 | 100 | 57 | 96 | 100 | 96 | 84 | 100 | 94 | 88 | | |
| C | 100 | 100 | 90 | 100 | 99 | 99 | 99 | 98 | 100 | 101 | 103 | 97 | 101 | 103 | 102 | 104 | 97 | 104 | 103 | 105 | 104 | 101 | | |
| D | 100 | 100 | 104 | 101 | 103 | 98 | 101 | 98 | 94 | 99 | 100 | 99 | 100 | 93 | 108 | 96 | 106 | 100 | 104 | 100 | 100 | 96 | | |
| E | 100 | 100 | 108 | 108 | 107 | 103 | 101 | 106 | 105 | 101 | 105 | 96 | 109 | 104 | 107 | 104 | 105 | 112 | 111 | 112 | 108 | 108 | | |
| F | 100 | 100 | 101 | 113 | 99 | 108 | 100 | 113 | 92 | 102 | 106 | 96 | 105 | 101 | 101 | 103 | 107 | 99 | 99 | 104 | 102 | 101 | | |
| G | 100 | 100 | 110 | 106 | 107 | 101 | 112 | 110 | 103 | 110 | 108 | 109 | 112 | 103 | 111 | 111 | 112 | 111 | 115 | 122 | 112 | 111 | | |
| H | 100 | 100 | 109 | 148 | 113 | 105 | 104 | 104 | 107 | 92 | 105 | 107 | 103 | 108 | 113 | 105 | 109 | 106 | 106 | 107 | 106 | 107 | | |
| I | 100 | 100 | 113 | 111 | 109 | 104 | 110 | 110 | 109 | 111 | 109 | 116 | 110 | 115 | 112 | 114 | 116 | 113 | 115 | 112 | 116 | 115 | | |
| J | 100 | 100 | 112 | 111 | 109 | 113 | 111 | 111 | 110 | 107 | 104 | 116 | 103 | 100 | 108 | 114 | 110 | 112 | 107 | 113 | 109 | 111 | | |
| K | 100 | 100 | 112 | 113 | 113 | 113 | 108 | 113 | 109 | 108 | 117 | 107 | 120 | 115 | 108 | 111 | 110 | 112 | 116 | 115 | 114 | 117 | | |
| L | 100 | 100 | 105 | 104 | 104 | 102 | 115 | 105 | 114 | 111 | 117 | 107 | 122 | 108 | 106 | 194 | 111 | 108 | 112 | 113 | 111 | 111 | | |
| M | 100 | 100 | 111 | 110 | 113 | 113 | 104 | 109 | 112 | 109 | 111 | 111 | 112 | 109 | 116 | 113 | 116 | 113 | 115 | 116 | 136 | 122 | | |
| N | 100 | 100 | 124 | 108 | 111 | 109 | 106 | 108 | 107 | 110 | 105 | 111 | 107 | 104 | 113 | 113 | 120 | 113 | 113 | 117 | 110 | 114 | | |
| O | 100 | 100 | 114 | 108 | 120 | 119 | 141 | 110 | 119 | 121 | 120 | 108 | 116 | 114 | 113 | 115 | 119 | 115 | 114 | 109 | 122 | 120 | | |
| P | 100 | 100 | 116 | 93 | 109 | 113 | 115 | 106 | 106 | 115 | 105 | 108 | 110 | 116 | 116 | 105 | 108 | 118 | 117 | 119 | 126 | 119 | | |
FIG. 5B
% Control Response | 0 | 17 | 33 | 50 | 67 | 83 | 100 | 117 | 133 | 150 | 167 | 183 |
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| A | 100 | 100 | 90 | 84 | 93 | 90 | 70 | 93 | 91 | 98 | 95 | 96 | 94 | 101 | 99 | 96 | 96 | 88 | 80 | 88 | 88 | 77 | | |
| B | 100 | 100 | 94 | 98 | 107 | 97 | 94 | 99 | 98 | 94 | 102 | 105 | 101 | 103 | 62 | 90 | 96 | 87 | 81 | 94 | 80 | 74 | | |
| C | 100 | 100 | 104 | 101 | 105 | 103 | 92 | 89 | 94 | 97 | 93 | 87 | 92 | 94 | 99 | 89 | 94 | 97 | 100 | 97 | 95 | 92 | | |
| D | 100 | 100 | 94 | 94 | 101 | 108 | 101 | 112 | 99 | 100 | 97 | 89 | 98 | 99 | 99 | 101 | 99 | 91 | 94 | 83 | 94 | 75 | | |
| E | 100 | 100 | 109 | 102 | 112 | 98 | 99 | 94 | 92 | 94 | 101 | 93 | 101 | 103 | 98 | 97 | 88 | 95 | 102 | 94 | 101 | 97 | | |
| F | 100 | 100 | 92 | 110 | 97 | 114 | 96 | 110 | 95 | 106 | 99 | 95 | 103 | 99 | 109 | 102 | 97 | 89 | 83 | 103 | 99 | 88 | | |
| G | 100 | 100 | 113 | 102 | 96 | 93 | 105 | 90 | 102 | 105 | 107 | 105 | 113 | 101 | 102 | 106 | 96 | 100 | 93 | 110 | 100 | 101 | | |
| H | 100 | 100 | 109 | 116 | 115 | 100 | 108 | 91 | 96 | 91 | 110 | 107 | 103 | 107 | 102 | 85 | 100 | 87 | 92 | 90 | 93 | 97 | | |
| I | 100 | 100 | 98 | 106 | 107 | 105 | 109 | 112 | 117 | 103 | 113 | 106 | 98 | 102 | 113 | 103 | 99 | 97 | 101 | 94 | 99 | 98 | | |
| J | 100 | 100 | 101 | 108 | 112 | 107 | 114 | 110 | 110 | 107 | 103 | 115 | 106 | 101 | 110 | 107 | 95 | 103 | 95 | 103 | 88 | 100 | | |
| K | 100 | 100 | 100 | 106 | 106 | 108 | 117 | 103 | 114 | 104 | 112 | 93 | 103 | 107 | 97 | 99 | 107 | 100 | 104 | 102 | 103 | 108 | | |
| L | 100 | 100 | 99 | 93 | 95 | 96 | 110 | 107 | 99 | 103 | 97 | 96 | 107 | 119 | 103 | 175 | 99 | 95 | 98 | 102 | 100 | 103 | | |
| M | 100 | 100 | 114 | 108 | 121 | 106 | 109 | 97 | 106 | 107 | 113 | 112 | 97 | 103 | 108 | 104 | 100 | 104 | 101 | 103 | 124 | 111 | | |
| N | 100 | 100 | 127 | 123 | 102 | 121 | 109 | 125 | 105 | 108 | 101 | 105 | 107 | 98 | 115 | 119 | 114 | 91 | 99 | 101 | 97 | 100 | | |
| O | 100 | 100 | 105 | 98 | 108 | 103 | 115 | 106 | 115 | 111 | 107 | 106 | 110 | 101 | 98 | 111 | 111 | 98 | 97 | 98 | 100 | 99 | | |
| P | 100 | 100 | 103 | 92 | 111 | 110 | 117 | 106 | 109 | 118 | 98 | 98 | 119 | 116 | 123 | 99 | 100 | 100 | 93 | 96 | 106 | 96 | | |
FIG. 5D

FLOW CYTOMETRY APPARATUS PULLING SAMPLE STREAM THROUGH OBSERVATION CHAMBER

CROSS-REFERENCE TO RELATED APPLICATION

This application is a division of application Ser. No. 12/802,880 filed 16 Jun. 2010 and claims the benefit of U.S. Provisional Patent Application No. 61/269,265 filed 22 Jun. 2009.

GOVERNMENT INTEREST STATEMENT

This invention is made with government support under contract number R01 HG005066 NIH and contract number U54 MH074425 NIH. The government has certain rights in this invention.

BACKGROUND OF THE INVENTION

This invention relates to flow cytometry.

Flow cytometers are frequently used for the analysis of particles such as cells or beads in a number of different applications. The system allows for determination of both particle morphology and evaluation of particle features by detection of optical labels. The ability to distinguish multiple particles sizes and colors allows multiplex application providing higher capacity of this technology to obtain information from analyzed targets.

The word "particle" as used herein means any discrete target that may be optically analyzed, enumerated or sorted by a flow cytometer. This group includes cells, cell fragments, and beads.

A conventional flow cytometry system disclosed in U.S. Pat. Nos. 6,315,952, 6,638,481, and 7,368,084 uses a positive pressure delivery system where a peristaltic pump injects samples into a flow cytometer. The pump is positioned between the microplate sample source and the cytometer, which has two significant consequences. First, it constrains the length of the sample tubing and fluid carryover (transfer of fluid between samples) that is directly proportional to tubing length. With a conventional HyperCyt® peristaltic pump and a sample tubing length of 1 M (0.01" ID), the fluid carryover between samples of 1-20 is about 10% based on the thin film left behind (J. W. Bartsch et al., Anal. Chem., 76:3810-17, 2004).

A second consequence of positioning a peristaltic pump between a sample source and a flow cytometer is that the passage of cells through the pump exerts compressive forces that can transiently perturb physiology (e.g., intracellular $Ca^{2+}$ equilibrium). The conventional HyperCyt® high-throughput flow cytometer system must therefore be limited in use to assays insensitive to such physiological perturbations.

SUMMARY OF THE INVENTION

There is a need for a high-throughput flow cytometry system that minimizes or at least reduces the length of tubing required between the samples and the flow cytometer.

There is also a need for a high-throughput flow cytometry system that may be used in assays that are sensitive to compressive pump forces on sample cells.

The present invention, therefore, contemplates the elimination of the peristaltic pump disposed between the sample source and the flow cytometer in prior art high-throughput flow cytometry systems, particularly the HypeCyt® high-throughput flow cytometer system.

To eliminate the need for an external peristaltic pump, the present invention directs the use of flow cytometers that do not require positive pressure for sample delivery and pull rather than push the samples through the observation chamber of the cytometer.

A flow cytometry apparatus in accordance with the present invention comprises a flow cytometer having a suction intake probe, a support for a microplate having a plurality of sample wells, and motive elements operatively connected to at least one of the probe and the support for moving the intake probe and the support relative to one another so that the intake probe is sequentially aligned with different sample wells of the microplate, there being an absence of fluid pumping elements between the support and the flow cytometer so that a bubble-separated sample stream is forced to the flow cytometer solely by virtue of a negative pressure communicated via the intake probe.

The intake probe, the support, and the motive elements cooperate to introduce aliquots of a separation fluid between successive samples from different wells of the microplate to generate the bubble-separated sample stream, the flow cytometer focusing (hydrodynamically or otherwise) the bubble-separated sample stream and selectively analyzing particles in each sample as the bubble-separated sample stream passes through the flow cytometer.

The support includes a microplate-holding stage and the motive elements controllably move the stage along three coordinate axes, such as orthogonal X, Y, and Z axes.

The support may incorporate three mechanical slides with stepper motors, the stepper motors being connected to a control unit that operates the stepper motors to incrementally move the stage so that the intake probe is sequentially aligned with different sample wells of the microplate. Each of the slides may be provided with at least one fixed end-of-travel limit switch for homing, that is, for establishing a fixed coordinate-axis reference point, and has a screw drive' actuator with a lead screw pitch of approximately 0.4 inches/revolution.

The apparatus may further comprising a plurality of risers or posts connected to the flow cytometer to elevate the flow cytometer above a horizontal support surface, the support and at least a portion of the support being disposable in a space between the flow cytometer and the horizontal support surface.

A flow cytometry apparatus comprises, pursuant to an embodiment of the present invention, a flow cytometer having a suction intake probe, a microplate support including a stage controllably movable along three coordinate axes, at least one motor operatively connected to the support for moving the stage along the three coordinate axes, and a control unit operatively connected to the motor for positioning the stage to sequentially align the intake probe with different sample wells of a microplate removably affixed to the stage. The apparatus has no fluid pumping elements upstream of the flow cytometer so that a bubble-separated sample stream is forced to the flow cytometer solely by virtue of a negative pressure communicated via the intake probe.

As generally discussed above, the microplate support may include three mechanical slides, the at least one motor being one of three stepper motors operatively connected to respective ones of the slides, the stepper motors being connected to a control unit that operates the stepper motors to incrementally move the stage so that the intake probe is sequentially aligned with different sample wells of the microplate.

Alternatively, the microplate support may be attached to a commercial autosampler capable of moving the support along three coordinate axes.

A kit for assembling a flow cytometry apparatus including a flow cytometer comprises, in accordance with the present invention, a plurality risers or posts attachable to the flow cytometer for elevating the flow cytometer a desired distance above a horizontal support surface, a microplate support including a stage controllably movable along three coordinate axes, the microplate support being disposable in a space below the elevated flow cytometer, and at least one motor operatively connected to the support for moving the stage along the three coordinate axes, the motor being operatively connectable to a control unit for operating the motor to position the stage so that the intake probe is sequentially alignable with different sample wells of a microplate removably affixed to the stage.

A method for operating a flow cytometry apparatus comprises, in accordance with the present invention, (a) supporting a microplate in juxtaposition to a suction intake probe of a flow cytometer, the microplate having a plurality of sample wells, (b) automatically and incrementally moving the microplate relative to the intake probe so that the intake probe is sequentially aligned with different sample wells of the microplate, and (c) feeding a series of bubble-separated samples from the different wells of the microplate to the flow cytometer via the intake probe, the moving of the series of the samples to the flow cytometer via the intake probe occurring solely under a negative pressure force exerted on the samples via the intake probe.

The moving of the microplate relative to the intake probe may include operating a plurality of stepper motors operatively connected to respective slides of a support assembly holding the microplate. The moving of the microplate may further include moving the slides along respective axes of a 3-axis coordinate system, including but not limited to an orthogonal XYZ coordinate system.

The present invention contemplates a miniaturized plate handling assembly, for instance, an automated XYZ stage as mentioned above, to replace the autosampler used in the conventional HyperCyt® high-throughput flow cytometer system. Alternatively, the conventional autosampler may be adapted to provide the basis of microplate manipulation. The XYZ stage is integrated with a flow cytometer that has a sample intake port that exerts a negative force (suction) on incoming samples. The suction intake port or probe aspirates samples from microplate wells, using its built-in negative-pressure sampling mode. This direct sampling technique can reduce the sample tubing path to less than 10 cm. A flow cytometer system in accordance with the present invention achieves significantly reduced fluid carryover, for instance, to possibly less than 1.0%.

A high-throughput flow cytometry system in accordance with the present invention greatly increases the sample throughput rate over conventional systems and may require only a single low-cost flow cytometer. The platform enables performance in a wider variety of specialized applications and secondary assays.

The present invention provides a flow cytometry system that may be used in assays involving viable cells, extending the range of assays amenable to high throughput flow cytometry analysis.

BRIEF DESCRIPTION OF THE DRAWINGS

FIGS. 3A, 3B, and 3C are graphs depicting an analysis of air-bubble-separated samples by an Accuri C6 flow cytometer.

FIGS. 5A-5G are graphs and tables or heatmaps depicting a screening platform comparison of the HyperCyt®/Cyan screening platform and a Velmex/Accuri C6 prototype platform. FIGS. 5A and 5C are graphs showing the resolution of four color-coded bead sets displaying 3 kinase target proteins (K2-wt, K2-mutant, K3-wt) or no target protein (scavenger) by the HCC (FIG. 5A) and VAC6 (FIG. 5C). FIGS. 5B and 5D are heatmaps of fluorescent K5 protein binding to K2-wt protein. FIGS. 5E-5G are correlation plots of the two screening platform determinations of K5 binding to K2-wt (FIG. 5E), K2-mutant (FIG. 5F), and K3-wt (FIG. 5G).

DETAILED DESCRIPTION

Figure 1:
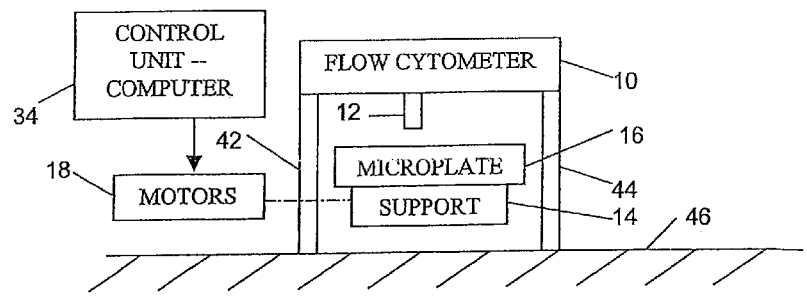
FIG. 1 is a block diagram of a flow cytometry apparatus in accordance with the present invention, showing in part a support for a multi-well microplate.

As depicted in FIG. 1, a flow cytometry apparatus with increased throughput comprises a flow cytometer 10 having a suction intake probe 12, a support 14 for a microplate 16 having a plurality of sample wells, and motive elements 18 operatively connected to at least one of the probe and the support for moving intake probe 12 and support 14 relative to one another so that the intake probe is sequentially aligned with different sample wells of microplate 16. There are no fluid pumping elements between support 14 and flow cytometer 10 so that a bubble-separated sample stream comprising a series of samples from different wells of the microplate is forced to the flow cytometer solely by virtue of a negative pressure communicated via intake probe 12.

Intake probe 12, support 14, and motive elements 18 cooperate to introduce aliquots of a separation fluid between successive samples from different wells of microplate 16 to generate the bubble-separated sample stream. Flow cytometer 10 focuses the bubble-separated sample stream and selectively analyzes particles in each sample as the bubble-separated sample stream passes through the flow cytometer.

In one implementation (FIG. 2), support 14 includes a microplate-holding stage 20. Motive elements 18 controllably move stage 20 along three coordinate axes, namely, orthogonal X, Y, and Z axes. To that end, support 14 incorporates three mechanical slides 22, 24, and 26 with respective stepper motors 28, 30, and 32 (motive elements 118). Stepper motors 28, 30, and 32 are connected to a control unit 34 in the form of a microprocessor or computer that operates the stepper motors to incrementally move stage 20 so that intake probe 12 is sequentially aligned with different sample wells of microplate 16. Each slide 22, 24, and 26 is provided with two fixed end-of-travel limit switches 35-40 and has a screw drive actuator (not shown) with a lead screw pitch of approximately 0.4 inches/revolution.

Figure 2:
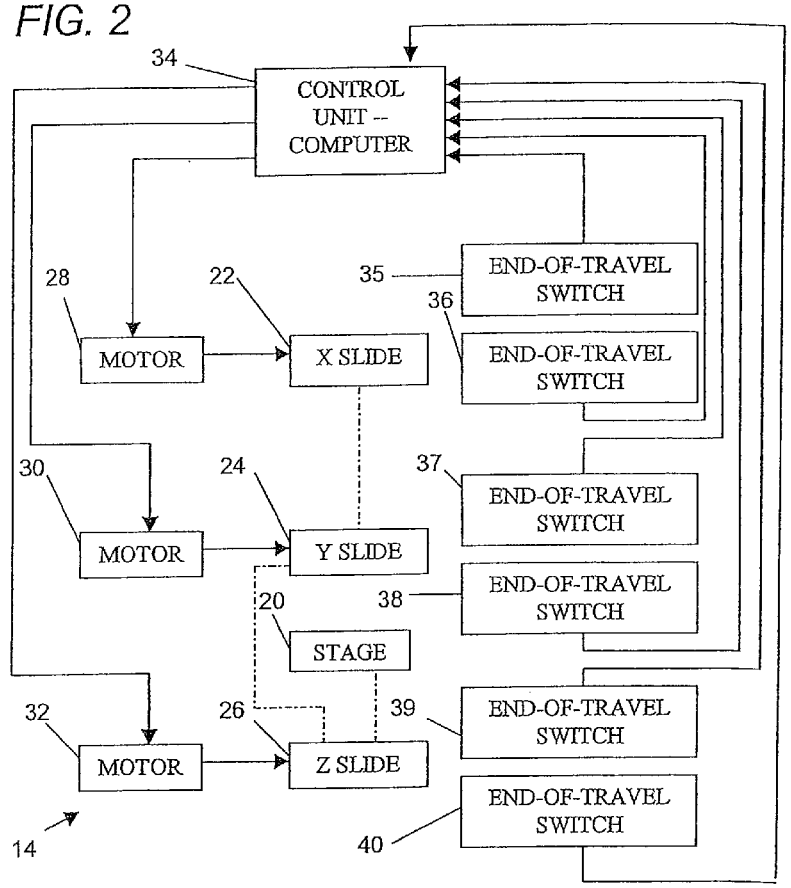
FIG. 2 is a block diagram of the microplate support of FIG. 1.

The flow cytometry apparatus of FIGS. 1 and 2 apparatus further comprises a plurality of risers or posts 42, 44 connected to flow cytometer 10 to elevate the flow cytometer above a horizontal support surface 46 such as a table top. Microplate 16 and at least a portion of support 14 are disposable in a space between flow cytometer 10 and horizontal support surface 46.

In the flow cytometry apparatus of FIGS. 1 and 2, stage 20 is controllably movable along three coordinate axes by the operation of stepper motors 28, 30, and 32 on slides 22, 24, and 26, under the control of computer or microprocessor 34. Computer or microprocessor 34 actuates stepper motors 28, 30, and 32 to incrementally reposition stage 20 to sequentially align intake probe 12 with different sample wells of microplate 16, which is removably affixed to stage 20. As there are no fluid-pumping elements upstream of the flow cytometer, the distance of travel between microplate 16 and flow cytometer 10 is minimized.

Support 14 is a miniaturized plate handling assembly in the form of an automated XYZ stage that replaces the autosampler used in the conventional HyperCyt® high-throughput flow cytometer system. The XYZ support 14 including stage 20 is integrated with flow cytometer 10, which has a sample intake port or probe 12 that exerts a negative force (suction) on incoming samples. Intake port or probe 12 aspirates samples from microplate wells, using a built-in negative-pressure sampling mode. This direct sampling technique can reduce the sample tubing path to less than 10 cm. The flow cytometer apparatus of FIGS. 1 and 2 achieves significantly reduced fluid carryover, to as little as or less than 1.0%.

Flow cytometer 10 may be implemented by an Accuri C6 flow cytometer, produced by Accuri Cytometers of Ann Arbor, Mich., USA. The Accuri C6 is an economical dual laser, six-parameter flow cytometer that has a sample intake probe that exerts a negative force (suction) on incoming samples. For less than 25% of the purchase price of other comparable instruments, the Accuri C6 has a performance that is comparable to other instruments. The Accuri C6 is useful in implementing flow cytometer 10, not only because of the C6's small size, low cost, and high performance, but because the C6 is able to aspirate samples directly without the need for a front-end peristaltic pump.

The Accuri C6 uses two peristaltic pumps working in tandem to produce a sample stream within an enveloping sheath stream. While this produces hydrodynamic focusing of the sample stream particles similar to conventional flow cytometry, the C6 uses negative pressure to pull both streams through the observation chamber, in contrast to a conventional positive pressure approach. It has been found that the aspiration of fluid samples via the suction intake probe of an Accuri C6 is compatible with a high-throughput screening (HTS) approach. First, it has been verified with an Accuri C6 that individual wells of a multiwell plate could be delivered manually with air bubbles inserted in the sample stream between sips (see FIG. 3). Particles in each bubble-separated sample were well aligned when the samples passed through the point of analysis. The pumps of the Accuri C6 are capable of generating significantly higher pressures to move the fluids at rates greater than 2 μl/sec to increase throughput. Also of importance is the unique ability of the Accuri C6 to coordinate the speed of the sheath stream pump with that of the sample stream pump to control the core diameter of the sample stream. This enables optimal particle alignment at the observation point even at high sample fluid flow rates.

Support 14 successively positions the wells of a microplate in the path of a C6 sample intake probe. Having the stage 20 capable of computer-controlled X, Y, and Z motions minimizes sample transit distances. As to speed and accuracy, the Velmex/Accuri C6 has better positioning precision than the LS-233 Gilson autosampler that has been conventionally used. However, other commercial autosamplers (including the Gilson GX274) may perform as well or better.

FIGS. 3A, 3B, and 3C are graphs depicting an analysis of air-bubble-separated samples by an Accuri C6 flow cytometer. A mixture of green fluorescent beads was sampled 9 times using the negative pressure sample uptake system of the C6 cytometer. Samples were aspirated by dipping the Accuri "sip" tube directly into the wells of the multi-well plate. An air bubble was aspirated between adjacent samples. The graph of FIG. 3A depicts a projection of bead distribution data along a time axis and shows good discrimination of each sample. FIG. 3B shows data projection along the green fluorescence intensity axis, revealing that seven distinct subsets of beads were resolved. Bead fluorescence intensity profiles within each sample were uniform and unperturbed by inter-sample bubble, as illustrated in FIG. 3C.

Figure 4:
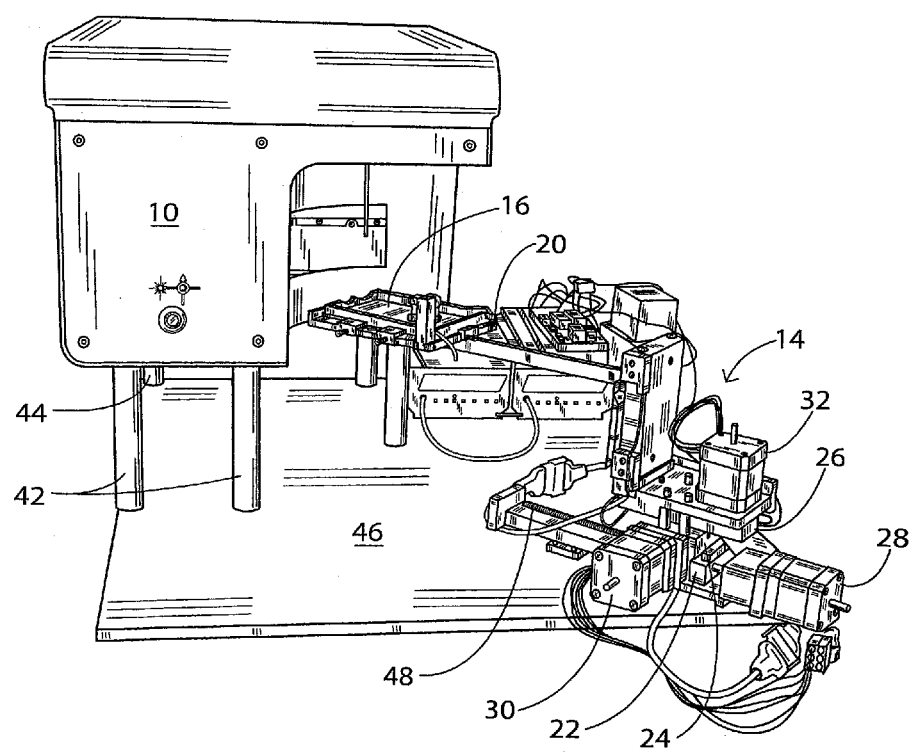
FIG. 4 is a perspective view of a particular embodiment of a flow cytometry apparatus in accordance with the present invention.

FIG. 4 depicts a particular embodiment of a high-throughput flow cytometry system, where reference numerals depicting specific implementations of the various elements of FIGS. 1 and 2 and designated by the same reference numerals. The embodiment of FIG. 4 includes miniaturized stage support assembly 14 including three mechanical slides 22, 24, 26 with respective stepper motors 28, 30, 32. Two slides 22 and 24 are positioned orthogonally in the horizontal plane (XY) and the third slide 26 (Z) is mounted perpendicularly to these. Each slide 22, 24, 26 is equipped with two fixed end-of travel limit switches 35-40 (FIGS. 1 and 2) and a screw drive actuator 48 with a lead screw pitch of 0.4 in/revolution. Stage 20 for mounting multi-well microplate 16 attaches to a mounting surface of the Z slide 26. The walls of the sample introduction chamber of an Accuri C6 flow cytometer 10 are provided with cutouts that allow the stage to perform the full range of motion required for positioning the sample uptake probe 12 in each well. The C6 cytometer 10 is elevated on 8-inch risers 42, 44 to accommodate slides 22, 24, 26 and motors 28, 30, 32 of support 14 below.

Stepper motors 28, 30, 32 may have Velmex stepper motor controllers capable of being operated in parallel, which can improve the efficiency of microplate positioning. For example, Z motion to move microplate 16 up to sample intake probe 12 of flow cytometer 10 can be actuated at a fixed point near the end of the X motion that positions the well beneath the probe. Likewise, X motion to position the next well can be actuated before the end of the subsequent downward Z-motion. Tests indicate that an operational platform with a theoretical performance limit of approximately 0.5 sec per well is attainable.

Platform Validation Experiments

To evaluate performance, the inventors analyzed a multiplexed bioassay in a 384-well plate format. The assay is a bead-based screen to identify small molecule regulators of protein interactions between K5 protein and kinase targets that physically interact with K5 in an intracellular signaling pathway. Targets include wild-type kinases K2 and K3 and a non-functional K2 mutant. Each is a biotinylated fusion protein that is attached to streptavidin-functionalized polystyrene beads. The assay measures the effect of test compounds on binding of a green fluorescent K5 peptide probe (AlexaFluo488-GST-K5 WT) to each target protein (530 nm emission, excitation at 488 nm). Beads for each target are pre-labeled with varying intensities of a red color, such that each assay is built on a unique bead set, and each bead set is associated with a unique optical address in the red fluorescence emission channel (750 nm, excitation at 635 nm). A streptavidin-only bead set control (no associated protein) is included as a scavenger assay to detect inherent green fluorescence properties of test compounds, a potential source of assay measurement artifacts. Each well contains all four bead sets, test compound and fluorescent K5 probe in a 10 μl volume.

Figure 5G:
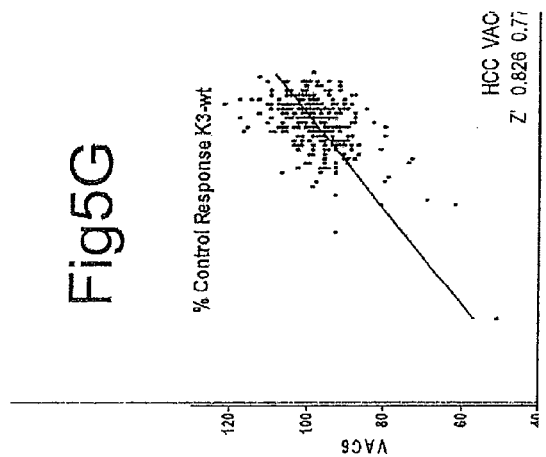
Figure 5F:
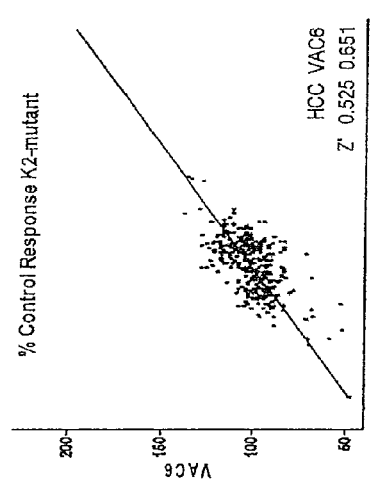
Figure 5E:
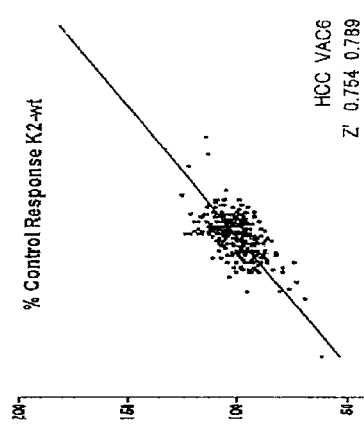

Each assay plate was first processed by a conventional peristaltic-pump-driven HyperCyt® screening platform using a Cyan flow cytometer for assay readout (HCC), then by the Velmex/Accuri C6 platform (VAC6). In plots of green vs. red fluorescence intensity the four bead sets were well resolved on both platforms (FIGS. 5A, 5C). Bead associated K5 fluorescence intensity in each well was normalized to results in control wells so that 100% represented no effect and values greater than and less than 100% represented activation and inhibition of K5 binding, respectively. Response distribution patterns were similar for both platforms, especially with compounds that produced the strongest responses (e.g., FIG. 5B vs. 5D, K2 results in wells B15 and L16). In correlation plots of K5 binding determinations from the two platforms (FIGS. 5E-5G), linear regression slopes for each target ranged between 0.88 and 0.97, consistent with response readouts of comparable magnitude over the measured range. Z' assay quality statistics ranged from 0.52 to 0.86 for the HCC and 0.65 to 0.79 for the VAC6 (FIGS. 5E-5G). Thus, the assay results were of comparable high quality for both platforms. In these validation tests the platforms processed the plates at similar speeds. However, there remains room for significant optimization of plate processing speed to improve performance of the VAC6 platform. Also, the inventors verified that the VAC6 could accurately position the Accuri sample intake probe in all wells of a 1536-well plate (data not shown).

Technological Innovation

The HyperCyt® high-throughput flow cytometer system represents a significant improvement for flow cytometry data acquisition over prior processing models, attaining multi-sample analysis rates 5- to 20-fold faster than any other flow cytometry technology on the market. The HyperCyt® high-throughput flow cytometer system routinely analyzes about 2,100 samples per hour in a 384 well format, a rate considered to be in the intermediate throughput range by industry standards. The present invention represents an alternative approach to increased throughput that offers several additional features. The novelty of the present approach resides in the adaptation of unique features of a negative-pressure-input flow cytometer (e.g., the Accuri C6). The invention takes advantage of a novel fluidics system whereby samples can be pulled rather than pushed through the observation chamber of a flow cytometer. Advantages include (1) elimination of cell exposure to compressive forces of the conventional HyperCyt® peristaltic pump, and (2) shortening of the sample transit distance 10-fold or more (from about one meter to less than 10 cm) to reduce fluid carryover between samples. The first advantage expands the repertoire of HTS-compatible assays to include compression-sensitive physiological responses (e.g., intracellular $Ca^{2+}$) while the second advantage reduces effects upon adjacent samples by compounds that are fluorescent or that induce perturbations within the context of a physiological measurement (e.g., signal transduction). A third source of anticipated improvement is an ability to maintain high precision optical resolution at increased sample flow rates, an attribute of the Accuri C6 fluidics system to control sample stream diameter.

FIGS. 5A-5G are graphs and tables depicting a screening platform comparison. A multiplexed K5 binding bioassay in a 384-well format was analyzed first with the HyperCyt®/Cyan screening platform (HCC) (FIGS. 5A and 5B) and then with a Velmex/Accuri C6 prototype platform (VAC6) (FIGS. 5C and 5D). Graphs in FIGS. 5A and 5C show the resolution of four color-coded bead sets displaying 3 kinase target proteins (K2-wt, K2-mutant, K3-wt) or no target protein (scavenger) by the HCC (FIG. 5A) and VAC6 (FIG. 5C). Heatmaps of fluorescent K5 binding to K2-wt protein (beads in gate 3) as determined by the HCC and VAC6 are shown in FIGS. 5B and 5D, respectively. Graphs of FIGS. 5E-5G are correlation plots of HCC vs. VAC6 determinations of K5 binding to K2-wt (FIG. 5E), K2-mutant (FIG. 5F), and K3-wt (FIG. 5G). Z' determinations for processing by each platform are indicated in the bottom right hand corners of the plots of FIGS. 5E-5G.

The flow cytometry apparatus of FIGS. 1-2 and 4 may be assembled from an off-the-shelf flow cytometer 10 and a kit comprising (i) a plurality risers or posts 42, 44 attachable to the flow cytometer for elevating the flow cytometer a desired distance above horizontal support surface 46, (ii) microplate support 14, and (iii) software for controlling the movement of slides 22, 24, 26 of support 14. Support 14 includes stage 20, slides 22, 24, 26, stepper motors, 28, 30, 32, and limit switches 35-40. The software is straightforward numerical control or robotic movement programming that operates motors 28, 30, 32 to step slides 22, 24, 26 along three coordinate axes so as to successively dispose different wells of microplate 16 below intake probe 12 of flow cytometer 10 after elevation thereof by means of risers or posts 42, 44.

A method for operating a flow cytometry apparatus such as that depicted in FIG. 4 comprises (a) supporting microplate 16 in juxtaposition to suction intake probe 12 of flow cytometer 10, (b) automatically and incrementally moving the microplate relative to the intake probe so that the intake probe is sequentially aligned with different sample wells of the microplate, and (c) feeding a series of bubble-separated samples from the different wells of the microplate to the flow cytometer via the intake probe, the moving of the series of the samples to the flow cytometer via the intake probe occurring solely under a negative pressure force exerted on the samples via the intake probe.

Although the invention has been described in terms of particular embodiments and applications, one of ordinary skill in the art, in light of this teaching, can generate additional embodiments and modifications without departing from the spirit of or exceeding the scope of the claimed invention. For example, although the present disclosure provides results specifically for an Accuri C6 flow cytometer, the present approach can be practiced with any flow cytometer that uses negative pressure to pull samples through the point of observation. Also other methods than hydronamic focusing are feasible for particle alignment in the flow cytometer (e.g., acoustic focusing). In addition, while switches are disclosed for limiting slide travel and establishing a coordinate reference point, other means known to those skilled in the art may be used instead. Also, while the pitch of the screw threads of the lead screw actuators 48 is disclosed hereinabove as having a pitch of 0.4 in/revolution, the pitch may be varied depending on the dimensions and distances, for instance, of the wells in microplate 16. Furthermore, the risers or posts 42, 44 used to enable free movement of microplate 16 below intake probe 12 can be replaced by other structural modifications as appropriate to enable well access to sample intake probe 12.

Accordingly, it is to be understood that the drawings and descriptions herein are proffered by way of example to facilitate comprehension of the invention and should not be construed to limit the scope thereof.

What is claimed is:

1. A method for operating a flow cytometry apparatus, comprising:
    supporting a microplate in juxtaposition to a suction intake probe of a flow cytometer, said microplate having a plurality of sample wells;
    automatically and incrementally moving at least one of said microplate and said intake probe relative to the other so that said intake probe is sequentially aligned with different sample wells of the microplate;
    extracting a liquid sample from each of the different sample wells of the microplate via said intake probe;
    introducing a separation fluid, different from the liquid of the extracted samples, between successive extracted samples to form a fluid-separated sample stream comprising a sequence of the extracted samples alternating in seriatim with the separation fluid;
    feeding said fluid-separated sample stream to said flow cytometer via said intake probe; and
    operating said flow cytometer and thereby focusing the fluid-separated sample stream and selectively analyzing particles in each sample as said fluid-separated sample stream passes through said flow cytometer,
    the extracting of the samples from the different sample wells and the moving of the samples in said fluid-separated sample stream to said flow cytometer occurring solely under a negative pressure force or vacuum exerted on said samples via said flow cytometer and said intake probe, no pump being disposed between said intake probe and said flow cytometer.

2. The method defined in claim 1 wherein the moving of said microplate relative to said intake probe including operating a plurality of stepper motors operatively connected to respective slides of a support assembly holding said microplate.

3. The method defined in claim 2 wherein the moving of said microplate includes moving said slides along respective axes of a 3-axis coordinate system.

4. A method for operating a flow cytometry apparatus, comprising:
    supporting a microplate in juxtaposition to a suction intake probe of a flow cytometer, said microplate having a plurality of sample wells;
    automatically and incrementally moving at least one of said microplate and said intake probe relative to the other;
    sequentially aligning said intake probe with different sample wells of the microplate;
    extracting a liquid sample from each of the different sample wells of the microplate via said intake probe;
    introducing a separation fluid between successive extracted samples to form a fluid-separated sample stream, wherein said separation fluid is different from the liquid of the extracted samples and wherein said fluid-separated sample stream comprises an in seriatim sequence of the extracted samples interleaved or alternating with the separation fluid;
    feeding said fluid-separated sample stream to said flow cytometer via a flow path extending from said intake probe to said flow cytometer; and
    in said flow cytometer focusing the fluid-separated sample stream and selectively analyze particles in each sample as said fluid-separated sample stream passes through said flow cytometer,
    the extracting of the samples from the different sample wells and the moving of the samples in said fluid-separated sample stream to said flow cytometer via said flow path occurring solely under a negative pressure force or vacuum exerted on said samples via said flow cytometer and said intake probe, no pump being disposed along said flow path.

5. The method defined in claim 4 wherein the moving of said microplate relative to said intake probe including operating a plurality of stepper motors operatively connected to respective slides of a support assembly holding said microplate.

6. The method defined in claim 5 wherein the moving of said microplate includes moving said slides along respective axes of a 3-axis coordinate system.

\* \* \* \* \*